United States Patent [19]

Nagai et al.

[11] 4,448,758

[45] May 15, 1984

[54] HYDROXYAPATITE, CERAMIC MATERIAL AND PROCESS FOR PREPARING THEREOF

[75] Inventors: Hirosi Nagai, Chofu; Yasushi Nishimura, Tokyo, both of Japan

[73] Assignee: Kureha Kagku Kagyo Kabushiki Kaisha, Tokyo, Japan

[21] Appl. No.: 318,020

[22] Filed: Nov. 4, 1981

Related U.S. Application Data

[62] Division of Ser. No. 188,832, Sep. 19, 1980, Pat. No. 4,330,514.

[30] Foreign Application Priority Data

Sep. 25, 1979 [JP] Japan .................................. 54-123000

[51] Int. Cl.$^3$ ................................................ C01B 25/32
[52] U.S. Cl. ..................................... 423/308; 423/309; 423/311; 433/199

[58] Field of Search ........................ 423/308, 309, 311

[56] References Cited

U.S. PATENT DOCUMENTS

| | | | |
|---|---|---|---|
| 3,379,541 | 4/1968 | Tuvell | 106/38.27 |
| 4,046,858 | 9/1977 | Barsa et al. | 423/305 |
| 4,097,935 | 7/1978 | Jarcho | 106/35 |
| 4,149,894 | 4/1979 | Ebihara et al. | 423/308 |

*Primary Examiner*—John Doll
*Assistant Examiner*—Wayne A. Langel
*Attorney, Agent, or Firm*—Wegner & Bretschneider

[57] ABSTRACT

This invention relates to hydroxyapatite, ceramic material, implant material and a process for preparing thereof. The ceramic material is hydroxyapatite ceramic having an excellent thermal stability.

1 Claim, No Drawings

HYDROXYAPATITE, CERAMIC MATERIAL AND PROCESS FOR PREPARING THEREOF

This application is a divisional of application Ser. No. 188,832 filed Sept. 19, 1980 now U.S. Pat. No. 4,330,514.

BACKGROUND AND DETAILED EXPLANATION OF THE INVENTION

The present invention relates to hydroxyapatite, ceramic material comprising hydroxyapatite ceramic and a process for preparing thereof. More in detail, the present invention concerns a colourless and translucent ceramic material of hydroxyapatite with a high density, a high purity and a high thermal stability, a process for preparing the same and a composition useful as an implant material comprising of the ceramic material and an organic binding material.

Hydroxyapatite is represented by the formula $Ca_{10}(PO_4)_6(OH)_2$ or $Ca_5(PO_4)_3(OH)$, and is one of the inorganic components of the hard tissues of living bodies such as bones, teeth, etc.

The sintered material of synthetic hydroxyapatite (hereinafter referred to as the ceramic material of hydroxyapatite) is, as has been published, usable as an implant material such as artificial dental root or artificial bone closely resembling those of living bodies (for instance, refer to Aoki and Kato, "Ceramic", 10(7): 469 (1975)), and it has been given attention, particularly in recent years.

Naturally, it is preferable that the synthesized ceramic material of hydroxyapatite resembles naturally occuring hydroxyapatite in physical properties. That is, the ceramic material of hydroxyapatite for use in living body is required to be colourless, to have a high density and to be safe for living bodies.

The purity concerning safety mentioned herein means the physicochemical purity. In other words, the purity of the ceramic material is determined by the facts that the material does not contain, as far as possible, the elements other than Ca, P or $PO_4$, and OH which are the substantial elemental components of hydroxyapatite; the Ca/P atomic ratio is close to 1.67 which is the theoretical value of hydroxyapatite and the physical structure is as close as possible to that of pure hydroxyapatite.

Among these factors, the defects in its physical structure, if any, can be detected by the X-ray analysis, and even in the case where its potential defects are not possibly detected, they may be detected clearly after treating the specimen at a high temperature of about 1350° C. The impurity which is apt to be frequently contained in the product of hydroxyapatite is whitlockite which has a lower value of Ca/P and a different physical structure and is highly soluble in aqueous solvent.

At any rate, the presence of these impurities and structural defects in and of the ceramic material makes the material coloured and eluted into within the living body to which the material has been applied. According to the one side of view points, it may preferable to have an accelerated substitution of the material with the tissues of the living body due to the above-mentioned elution, however, from the other side of view points, safety, there may be unfavorable effects on the living body due to the topical electrolyte imbalance caused by the elution and to the harmful action, etc. of the eluted substance itself.

Accordingly, it is strongly demanded that the ceramic material of hydroxyapatite is highly pure as well as it is almost colourless and in high density, and accordingly, it is very important to offer its industrial process for preparing such a favorable ceramic material. However, as will be shown below, under present conditions, such a ceramic material satisfying the above-mentioned demands has not been completed yet.

A number of processes for synthesizing hydroxyapatite have been proposed, for instance, by R. W. Mooney, et al., "Chem. Rev.," 61:433(1961) and by Kanazawa, et al., "Kagaku no Ryoiki," 27:622(1973). However, there are few disclosures which have discussed the process for preparing a ceramic material comprising the firing of the above-mentioned hydroxyapatite. Among them, Monreo reported that he has obtained a ceramic material by compression-molding powdery hydroxyapatite and then firing the thus molded material at a temperature of 1300° C. under normal pressure (refer to "J. Dent. Res.," 50,860(1971)). However, since his ceramic material contains as high as 30% by weight of whitlockite (alpha-calcium triphosphate), it cannot be said the ceramic material of highly pure hydroxyapatite.

The reason why the ceramic material of highly pure hydroxyapatite has not been available is considered to be the fact that the hydroxyapatite used for making the material had not the correct stoichiometrical composition or it had some structural defects resulting in the by-production of whitlockite at the time of firing, which has a different structure. In these considerations, a trial has been carried out wherein the hydroxyapatite of the correct stoichiometric composition was synthesized and then the hydroxyapatite was fired. However, the hydroxyapatite hitherto obtained by the conventional process for synthesis was poor in sintering property and in thermal stability due to its problems of purity, its own crystalline structure and the morphological problem of its own crystalline particles. Accordingly, the thermally stable ceramic material with a high density and a high purity has not yet been obtained. For instance, although the Japanese Patent Application Laying Open No. 64199/77 offers a method of adding foreign metals such as MgO, etc. In order to improve the insufficient sintering property of the precursor of the ceramic material having the stoichiometrical composition of hydroxyapatite available by the conventional synthetic process, the above-mentioned method was based on the positive introduction of foreign elements for the purpose of improving the sintering property of the precursor, and accordingly, was completely different from the present invention in its idea, as will be described later.

On the other hand, M. Jarcho used a method by Haek (refer to Angew. Chem., 67:327 (1955) and Inorg. Synt., 7:63 (1963)) based on the following reaction:

in which calcium nitrate is brought into reaction with diammonium hydrogen phosphate while regulating the pH of the reaction system at 10 to 12 with the addition of ammonia to synthesize hydroxyapatite. The cake-like hydroxyapatite obtained by filtrating the reaction mixture is then fired at a temperature of 1100° to 1200° C.

It was reported that a ceramic material of hydroxyapatite having a mean size of crystals of about 0.2 to 3 microns and of 3.10 to 3.14 g/cm³ in density was obtained by the above-mentioned procedures (refer to U.S. Pat. No. 4,097,935, Japanese Patent Applications Nos. 40400/76, 94309/77 and "J. Material Sci.," 11:2027(1976)).

However, it was disclosed in the above-mentioned literature that the ceramic material of hydroxyapatite was partially decomposed to a by-product, whitlockite, in the case where it was treated at a temperature of higher than 1250° C. for more than one hour. That is, the ceramic material of hydroxyapatite obtained by the above-mentioned procedures still contains a structurally unstable factors, in other words, has substantially structural defects, and accordingly, is poor in thermal stability. In addition, there is a difficulty to remove by-producing ammonium nitrate.

Further, as a different method for synthesizing hydroxyapatite, a method utilizing the following reaction of calcium hydroxide with phosphoric acid has been disclosed:

$$5Ca(OH)_2 + 3H_3PO_4 \rightarrow Ca_5(PO_4)_3(OH) + 9H_2O.$$

The above-mentioned reaction is expected to develop into an industrial method for producing hydroxyapatite of the correct stoichiometric composition because of (1) not containing any foreign elements and (2) having only water as a by-product, however, Mooney said in his article "Chem. Rev.," 61,433(1961) that it was difficult to obtain the hydroxyapatite of stoichiometric coompoosition (theoretical value of Ca/P atomic ratio of 1.67) by the above-mentioned reaction, and only the hydroxyapatite of Ca/P of 1.50 corresponding to calcium triphosphate was obtainable.

On the other hand, R. Wallaeys (refer to "Angew. Chem. (Paris)," 7,808 (1952)) obtained the hydroxyapatite of Ca/P atomic ratio of 1.61 to 1.67 by boiling the above-mentioned reaction mixture after the reaction was over in order to make the reaction proceed completely or making the reaction proceed to the neutral point to phenolphthalein in a boiling state.

However, according to the results of trace-experiments of the method of Wallaeys carried out by the inventors of the present invention it was found that the dried material of filtered cake of hydroxyapatite obtained by the Wallaeys's method was poor in sintering property and accordingly, only a ceramic material having a density of about 3.11 g/cm³ was obtained even by the hot-press method at a high temperature, and moreover, the thus obtained material was coloured in blue after sintering. The cause of colouring is not yet elucidated, however, it may be considered to be due to some structural defects as a ceramic material in addition to the presence of a minute amount of impurities. As mentioned above, it was clearly found that the method of Wallaeys could not satisfy the purpose of the present invention.

As has been described above, the publicly known ceramic material of hydroxyapatite contains foreign elements for the improvement of the sintering property of synthetic hydroxyapatite, or has structural defects causing the poor thermal stability and is coloured when sintered. In other words, under the present conditions, a highly pure and highly stable ceramic material of a high density of hydroxyapatite suitable for application into living bodies and its effective method for preparing thereof have not been completed.

The inventors of the present invention, while taking into consideration of the above-mentioned status quo, studied the relationship between the sintering property or the thermal stability of the ceramic material and the crystalline form and shape and the structure of synthetic hydroxyapatite, and have found that a ceramic material excellent in thermal stability, colourless, having a high purity and a high strength without any structural defects which does not decompose to form whitlockite even after heating for one hour at a temperature of 1350° C. is obtained by firing a dried cake after filtration of synthetic hydroxyapatite of the stoichiometric composition having a specified properties, and they have arrived at the present invention.

It is an object of the present invention to provide a filtered, dried cake of hydroxyapatite having a structure possessing the three-dimensional order with an average opening radius of 50 to 150 Å and a pore cavity of 0.2 to 0.8 cm³/g, said cake comprising, hydroxyapatite having an atomic ratio of calcium to phosphorus of 1.67 to 1.69 and a dimension including a length of 150 to 1200 Å, a width of 50 to 400 Å, a ratio of said length to said width of 3 to 10. Another object of the invention is to provide a ceramic material comprising hydroxyapatite ceramic having an atomic ratio of calcium to phosphorus of 1.67 to 1.69, an average crystal size of 4 to 20μ, a density of 3.14 to 3.16 g/cm³ and a thermal stability wherein whitlockite is not shown after said hydroxyapatite ceramic is heated for at least one hour at a temperature of 1350° C., said ceramic being colourless or semi transparent. A further object of the invention is to provide an implant material comprising both ceramic material of hydroxyapatite and a bonding material having a biological acceptability to living body. A particular object of the invention is to provide process for preparing hydroxyapatite, comprising the steps of, (a) converting powder calcium carbonate into calcium oxide by thermal decomposing in an inert atmosphere at a tempearture of 800° to 1300° C. for 0.5 to 10 hours, (b) cooling the converted calcium oxide to a temperature lower than 500° C. in the inert atomosphere to obtain extremely porous high reactive calcium oxide, (c) slaking the cooled calcium oxide with water while agitating under turbulent flow thereby to obtain fairly fine calcium hydroxide milk of high purity, (d) bringing the obtained calcium hydroxide into reaction with an aqueous solution of phosphoric acid in an inert atmosphere under turbulent flow, thereby to obtain hydroxyapatite.

According to the present invention, that is, when an aqueous emulsion of minute particles of calcium hydroxide formed by bringing porous and minute particles of practically pure calcium oxide into reaction with an excess amount of water is brought into reaction with an aqueous solution of phosphoric acid in an inert atmosphere, a milky reaction mixture containing the reaction product, hydroxyapatite is obtained.

After filtering the milky reaction mixture, the separated cake is washed with water and dried to be an aggregate of hydroxyapatite having the following properties:

Analytical value of an atomic ratio of Ca/P: 1.67 to 1.69,

Mean size of dimension of hydroxyapatite of:
length: 150 to 1200 Å
width: 50 to 400 Å, and
ratio of lengh/width: 3 to 10.

Void: 0.2 to 0.8 cm$^3$/g

Mean pore-radius: 50 to 150 Å.

By firing the above-mentioned filtered cake, the aggregate of hydroxyapatite, a ceramic material of hydroxyapatite having the following physical properties is obtained:

Analytical value of Ca/P: 1.67 to 1.69,
Mean crystal size: 4 to 20 microns, and
Density: 3.14 to 3.16 g/cm$^3$.

The fact that the mean crystal size of the thus obtained material is larger than that of the conventional synthetic ceramic material of hydroxyapatite means that the ceramic material of the present invention is prepared from the purer raw materials than those used for preparing the conventional materials. In addition, the fact that even after firing of the aggregate of hydroxyapatite at a temperature of 1350° C. for one hour, any formation of whitlockite which is the decomposition product of hydroxyapatite is not recognized this fact that some components or structural defect including the decomposition are not contained therein and the aggregate is excellent in thermal stability.

The followings are the more detailed explanation of the the present invention:

The porous and minute particles of calcium oxide for use in the process of the present invention is obtainable by thermally decomposing powdery calcium carbonate. As the raw material, calcium carbonate is preferably in a high purity of higher than 99.0%, preferably 99.8% and in a micro-fine state. The conditions of thermal decomposition are: in an inert atmosphere, at a temperature of 800 to 1300° C., preferably 950° to 1200° C., for 0.5 to 10 hours, preferably one to five hours. By the decomposition under the above-mentioned conditions, calcium carbonate is converted to highly porous and reactive fine powder of calcium oxide while leaving gaseous carbon dioxide free.

In this case of thermal decomposition, the milder conditions of thermal decomposition lead to the remaining of undecomposed calcium carbonate in the produced calcium oxide. Not only it is difficult to remove the remaining calcium carbonate in the produced calcium oxide, but also the remaining calcium carbonate becomes to be a cause of the structural deffects and the reduction of the thermal stability of the ceramic material of hydroxyapatite which is one of the final products of the present invention. In addition, in the case where the conditions of thermal decomposition is more severe or in the case where the product of the thermal decomposition is not cooled in an inert atmosphere until the temperature of the product is fallen to 500° C., preferably to 200° C., the porosity and the reactivity of the thus produced calcium oxide are impaired. In this connection, the inert atmosphere herein mentioned means the atmosphere which does not contain any components inducing the secondary reaction with the produced calcium oxide and calcium hydroxide, such as gaseous carbon dioxide and ammonia.

It is effective to blow an inert gas such as nitrogen, helium, argon, etc. into the system of thermal decomposition in order to obtain the inert atmosphere because gasenous carbon dioxide thus generated is successively removed from the system.

The aqueous emulsion of minute particles of calcium hydroxide of the present invention is, as mentioned above, possibly produced by adding the above-mentioned calcium oxide into a large amount of water in a state of high speed stirring to provide turbulent flow under the above-mentioned inert atmosphere. In this case, the amount of water which is mixed with one part by weight of calcium oxide is not limited, however, usually it is 10 to 100 parts by weight.

The above-mentioned reaction is carried out under a high speed stirring, preferably at a relatively low temperature for a relatively long time period and usually at 0 to 80° C., preferably 0 to 50° C., for 0.5 to 96 hours, preferably one to twenty four hours.

The end point of the above-mentioned reaction is determined by X-ray diffraction analysis, wherein a part of the reaction product is withdrawn as a specimen and the disappearance of d$_{200}$ in the X-ray diffraction pattern of the specimen is taken as the sign of the completion of the reaction.

In addition, the mean size of particles of calcium hydroxide prepared by the method of the present invention is 0.05 to 0.1 micron and it is far smaller than the mean size of calcium hydroxide particles of one to ten microns, which are obtained by dispersing commercial calcium hydroxide into water.

The above-mentioned emulsion of fine particles of calcium hydroxide is the important requisite for obtaining the hydroxyapatite with a favorable sintering property described later.

The hydroxyapatite according to the present invention is formed in a milky state by adding an aqueous solution of phosphoric acid in an amount corresponding to Ca/P of 1.67 to 1.69 into the above-mentioned aqueous emulsion of minute particles of calcium hydroxide in a state of high speed stirring under the inert atmosphere to be brought into reaction.

In the preparation of the hydroxyapatite, it is preferable that the stirring is still continued after completing the reaction of formation of the above-mentioned emulsion of calcium hydroxide, and the aqueous solution of phosphoric acid is added successively into the system under stirring.

Phosphoric acid is usually made to be an aqueous one to ten percent by weight solution and the solution is slowly added to the above-mentioned emulsion. In this connection, the high speed stirring referred herein means the stirring which brings the state of the liquid in the reaction system into a turbulent flow.

The reaction temperature is 0 to 50° C. At a lower temperature, the viscosity of the emulsion is so high that the uniformal reaction becomes difficult, and at a higher temperature, the sintering property of the above-mentioned aggregate of hydroxyapatite is impaired. Thus, the reaction temperature is an extremely important factor affecting the size of crystals concerning the sintering property or affecting the easily sedimenting property which will be described later. The reaction is usually carried out for 0.5 to 200 hours, preferably for 5 to 100 hours. The reaction mixture is highly alkaline of pH of about 13 at an initial stage and the alkalinity is gradually reduced to pH of 8 to 9 at the completion of the reaction.

Although hydroxyapatite in the reaction system assumes a milky state, it is excellent in sedimentability the easily separable by filtration, microscopically the size of the hydroxyapatite being, as has been described, usually of 50 to 400 Å in width, 150 to 1200 Å in length and the ratio of length to width of 3 to 10.

These dimensions are clearly differ from those of the plate-like crystal of about 200 Å in width and about 200 Å in length obtained by the aforementioned reaction between calcium nitrate and diammonium hydrogen phosphate. The easy sedimentability of the hydroxyapatite obtained by the process of the present invention is considered to be due to such a size of crystals, their shape and form and further to the state of electric charge on the surface of the crystals. Moreover, these factors presumably contribute the formation of the aggregate of hydroxyapatite of the present invention, which has a favorable sintering property.

The aggregate of hydroxyapatite according to the present invention is obtained by filtering hydroxyapatite obtained by the above-mentioned method to a water content of about 0 to 2% by weight. The thus obtained cake of aggregate of hydroxyapatite has the following physical properties of: said cake possessing a void ratio of 0.2 to 0.8 cm$^3$/g and pore radius of 50 to 150 Å, comprising hydroxyapatite having a Ca/P atomic ratio of 1.67 to 1.69, crystal size of 50 to 400 Å in width, 150 to 1200 Å in length, the ratio of width to length of 3 to 10, and these properties affect the specific properties of the ceramic material of hydroxyapatite described later.

The aggregate of hydroxyapatite according to the present invention has a favorable sintering property and when firined as it is, a ceramic material having an excellent property is obtained as will be shown later.

Naturally, conventional methods for molding and firing the aggregate are applicable in preparing the ceramic material according to the present invention, fro instance, the aggregate may be molded by using a metal or rubber mold and then baked, or the aggregate may be molded and fired by a hot press method or the molded cake can be fired under a reduced pressure.

In addition, a ceramic material highly translucent, highly pure, highly dense and highly stable thermally is also available by firing under reduced pressure after pressure-molding the aggregate of hydrioxyapatite according to the present invention. The condition of baking are: at a temperature of 850° to 1400° C., preferably 1250° to 1400° C., for 0.5 to 5 hours, preferably 1 to 3 hours. In addition, it is noticed that the growth of the crystals of the hydroxyapatite of the present invention during the sintering by firing is remarkably larger than that of the conventional hydroxyapatite. Such a property is presumably due to the above-mentioned specific properties of the aggregate of hydroxyapatite and its favorable sintering property.

The ceramic material of hydroxyapatite prepared according to the present invention has the following properties of:

(a) analytical Ca/P: 1.67 to 1.69,
(b) mean size of crystals: 4 to 20 microns,
(c) density: 3.14 to 3.16 g/cm$^3$, and
(d) thermal stability: no formation of whitlockite is recognized after heating for one hour at 1350° C.

While the publicly known ceramic materials of hydroxyapatite form whitlockite when heated at a temperature of higher than 1200° C. or 1300° C., the ceramic material according to the present invention is extremely stable at a temperature of higher than 1300° C., and the size of crystals of the material according to the present invention is larger than that of the publicly known ceramic material of hydroxyapatite, the former being clearly differentiated from the latter.

The ceramic material according to the present invention is excellent in stability whithin the living body presumably due to the absence of structural defects. In addition, the ceramic material of the present invention can be prepared by the successive steps of drying and firing in the order, cake obtained by filtration of the afore-mentioned reaction solution.

The thermal stability of the above-mentioned ceramic material is confirmed by the determination of X-ray diffraction pattern after sintering the material for one hour at a temperature of 1350° C.

As has been described, according to the present invention, the hydroxyapatite excellent in sintering property and stoichiometric in composition is easily available by bringing a specified calcium hydroxide into reaction with phosphoric acid under mild conditions, and so the process of the present invention is extremely effective as an industrial method. Moreover, the ceramic material of hydroxyapatite obtained by the present invention is chemically and physico-structurally pure and stable enough to be used within living bodies and useful as an implant material such as artificial dental roots and artificial bones.

In the next place, in the practical application of the ceramic material of hydroxyapatite as an implant material, particularly as an artificial dental root material, the material can be applied by the following method. The ceramic material may be solely utilized for an implant material.

The implant material according to the present invention is prepared, in consideration of its processability, easiness of handling and mechanical strength, by molding the mixture of the above-mentioned hydroxyapatite of a particle size smaller than 1000 microns, preferably 0.01 to 100 microns and an organic matrix, in a publicly known process, or by impregnating the organic matrix into the porously formulated ceramic material of the present invention. In the process of preparing the implanting material, it is important that the ratio of surface area of the hydroxyapatite phase of the implant material to that of organic matrix of the implanting material in the adhering surface to the bone is processed to be 5:95 to 70:30, preferably 10:90 to 60:40. In the case where the phase of hydroxyapatite occupies more than 70% of the surface area of the above-mentioned adhering surface, the adhesion to the natural bone is too large necessitating the impairment of the natural bone when the implanted material is to be removed. However, in the case where the above-mentioned phase occupies less than 5% of the surface area of the adhering surface, the implanted material is apt to be naturally removed. The above-mentioned ratio has been decided in consideraiton of the durability and adhesiveness of the artificial dental root.

An organic polymeric binding material is referred to the organic matrix. As the organic material, since it is necessary to use a non-deteriorative resin for the long term implantation in living body without degrading the cells of the living body, one or a mixture of more than one substance selected from the group consisting of polycondensate of bisphenol A and glycidyl methacrylate, poly(methyl methacrylate), poly(2-hydroxyethyl methacrylate), poly(triethyleneglycol dimethacrylate), polyethylene, polysulfone resin, polyamide resin, polyester resin, poly(tetrafluoroethylene), poly(vinylidene fluoride) and polycarbonate resin, or copolymers comprising more than one monomer which constitute the above-mentioned polymers is preferable.

In addition, the ceramic material of the present invention is used as a component of the material usable within living body such as the co-existent-type sintered material with an organic substance such as cellulose, collagen, etc., the porous material prepared by boring, the composition prepared by impregnating an organic resin, or impregnating and polymerizing an organic monomer into the porous material, the composite of the powdery ceramic material with an organic or inorganic matrix or their combination.

Moreover, the hydroxyapatite according to the present invention can be used as a filling material for the chromatographic column, other than the use of them as the baked material.

The present invention will be further described in more detail while referring to non-limitative examples as follows:

EXAMPLE 1

Into an electric furnace under a flow of gaseous nitrogen of a flow rate of one liter/min, 600 g of powdery calcium carbonate of reagent grade (G.R.) were introduced and heated to a temperature of 1000° C. at a rate of 3° C./min. After heating for 3 hours at 1000° C. to decompose the material, it was cooled under the flow of gaseous nitrogen to 200° C. at a rate of one liter/min to obtain 335 g of calcium oxide with a yield of 99.7%. It was confirmed that the thus obtained calcium oxide did not contain calcium carbonate, by X-ray diffraction analysis. The purity of the product determined by ED-TA-method was 99.8%. According to microscopical observation, the crystal shape of the obtained calcium oxide was similar to that of the raw material, calcium carbonate, and the crystal of the calcium oxide was porous.

Into a 17-liter three necked porcelain enameled tank provided with a heater, a temperature-controller and a thermometer, 6 liters of de-aired distilled water were introduced, the atmosphere in the tank was substituted by nitrogen while agitating at a revolution of 350 rpm. Then, 280 g (5 mol) of the above-mentioned calcium oxide were slowly added within 10 minutes, and then made to react for 5 hours at 50° C., and for 15 hours at room temperature under the atmosphere of gaseous nitrogen to obtain an emulsion of calcium hydroxide of 0.075 micron in mean particle diameter.

In the next place, while keeping the thus obtained emulsion at a turbulent flow by agitation of 3000 rpm, three mols of an aqueous 3.5% solution of phosphoric acid prepared from 85% phosporic acid, were added to the emulsion within 30 min, and then the reaction was continued for 48 hours at a temperature of 20° C. After the reaction was over, the thus obtained suspension was filtered under pressure, the residue being washed with water and dried at 150° C. for 16 hours.

Thus, 497 g of the dried material of filtered cake of hydroxyapatite were obtained and named as Specimen No. 1, the properties of the dried material, that is, the aggregate of hydroxyapatite of the present invention being shown in Table 1.

EXAMPLE 2

Another aggregate of hydroxyapatite of the present invention named as Specimen No. 2 was prepared by the same procedure as in Example 1 except for the reaction condition of a temperature of 40° C. and for 24 hours as compared to the temeperature of 20° and for 48 hours in Example 1. The thus obtained Specimen No. 2 showed the properties also shown in Table 1.

COMPARATIVE EXAMPLE 1

An aqueous dispersion prepared by adding 5 mols of powdery calcium hydroxide of reagent grade (G.R.), into 6 liters of de-aired distilled water was introduced in the porcelain enamaled tank used in Example 1, and while agitating at a revolution of 3000 rpm under the substituted nitrogen atmosphere by a flow of gaseous nitrogen, 3 mols of an aqueous 3.5% solution of phosphoric acid were slowly added to the dispersion. After carrying out a reaction at a temperature of 70° C. for 24 hours, the same procedures as in Example 1 were taken to obtain an aggregate of hydroxyapatite named as Specimen No. 3, the properties of Specimen No. 3 being shown also in Table 1.

COMPARATIVE EXAMPLE 2

Another aggregate of hydroxyapatite named Specimen No. 4 was prepared by the following publicly well known method and its properties were also shown in Table 1.

Diammonium hydrogen phosphate (160 g) was dissolved into distilled water (3 liters) and an aqueous 28% ammonic solution (1700 ml) was added to the above-mentioned solution to adjust the pH at 11 to 12. Distilled water was further added to it to dissolve the thus precipitated diammonium hydrogen phosphate. This solution was poured into a solution prepared by dissolving 477 g of calcium nitrate into 188 ml of distilled water adjusted to pH of 12 by an addition of 60 ml of a concentrated aqueous ammoniac solution and kept at a temperature of 20° C. under a high speed stirring within 30 min. The mixture was further diluted with distilled water until the whole volume arrived at 7.0 liters. After boiling the thus diluted solution for 10 min, it was left at room temperature for 20 hours.

The thus produced gelatinous material was filtered by Buchner's funnel under slightly reduced pressure, washed with water while kept on the filter, and when cracks appeared on the surface of the filtered cake, the higher vacuum was applied for 2 hours. The filtered cake was dried at 150° C. for 15 hours to obtain 197 g of an aggregate of hydroxyapatite.

EXAMPLE 3

Respective specimens of aggregates of hydroxyapatite obtained by Examples 1 and 2 and Comparative Examples 1 and 2 were placed in an electric furnace and heated to a temperature of 1350° C. at a rate of 3° C./min. After keeping at the temperature for one hour, it was removed from the furnace to be cooled to room temperature. The thus obtained ceramic materials had their respective specific properteis shown in Table 2.

Respective ceramic materials were crushed to pieces of about 5 mm in size, and after immersing the pieces into an 0.1% aqueous solution of neutral red at room temperature for 15 hours, the pieces were washed with water and dried to examine the coloration of their respective surface of crushing. The results of the examination showed that although no coloration was observed on Specimens No. 1 and No. 2 of Examples 1 and 2, a coloration was observed on Specimen No. 4 of Comparative Example 2. Since Specimen No. 3 showed a blue colour before immersing into the solution of the dye-staff, it could not be compared. From these results it was clear that the ceramic material of the present invention differs from the publicly known ceramic material.

EXAMPLE 4

Twenty grams of the aggregate of hydroxyapatite of the present invention obtained in Example 1, Specimen No. 1, were fired at a temperature of 1250° C. under a reduced pressure of $10^{-2}$ mmHg for one hour, and cooled to 200° C. under the reduced pressure to prepare a ceramic material. The thus prepared ceramic material was white in colour, transparent and showed a density of 3.16 g/cm$^3$ which is the theoretical value.

EXAMPLE 5

Sintering test was carried out on the aggregates of hydroxyapatite of Specimen No. 1 of Example 1 and Specimen No. 4 of Comparative Example 2. Each 20 g of Specimens was baked at each temperature of 1200°, 1250°, 1300° and 1350° C. for one hour, and the amount of whitlockite formed within the fired material was determined by X-ray diffraction analysis. The results are shown in Table 3. As is seen in Table 3, the difference between the ceramic material according to the present invention and the publicly known ceramic material is clear.

EXAMPLE 6

The ceramic material prepared in Example 3 from Specimen No. 1 was pulverized and the fraction passed through a sieve of 200 mesh was collected. The thus collected powdery material was mixed with a 6:4 by weight mixture of copolymer of bisphenol A and glycidyl methacrylate and monomeric methyl methacrylate at a volume ratio (calculated by the respective weights and densities of both components) of 1:1, and after the further addition of 0.05% by weight of benzoyl peroxide as a polymerization initiator, the mixture was mixed to be uniform, and after pouring into a glass tube of 5 mm in inner diameter and de-bubbling, a polymerization was carried out at 80° C. for 2 hours on the mixture to obtain a composition of hydroxyapatite. After processing the composition into a cylinder of 3.5 mm in diameter and 10 mm in length, it was implanted into the drilled hole of the jaw-bone of an adult dog just after the tooth extraction. The implanted material was not naturally removed even after 3 months of implantation. After 6 months of implantation, the jaw-bone of the dog was cut off to be examined by an optical microscope and roentgenography. It was found that the implanted part was normally healed and a new bone-tissue was produced within the gap between the implanted composition and the jaw-bone.

TABLE 1

| | | | | Properties of Aggregates of hydroxyapatite | | | | | | |
|---|---|---|---|---|---|---|---|---|---|---|
| | | Reaction | | | | | Size of crystal | | | |
| Classification | Specimen No. | time (hour) temp. (°C.) | Yield (%) | Elementary analysis | | | length L (Å) | width W(Å) | L/W | Void volume[1] (ml/g) | Pore-radius[2] (Å) |
| | | | | Ca (%) | P (%) | Ca/P | | | | | |
| Theoretical | | | | 39.89 | 18.43 | 1.67 | | | | | |
| Present invention | 1 | 48 20 | 99 | 39.75 | 18.43 | 1.67 | 900 | 80 | 3.75 | 0.47 | 100 |
| | 2 | 24 40 | 99 | 39.80 | 18.46 | 1.67 | 900 | 200 | 4.50 | 0.65 | 140 |
| Comparative | 3 | 24 70 | 99 | 39.78 | 18.45 | 1.67 | 2300 | 350 | 6.25 | 0.88 | 400 |
| | 4 | 24 20 | 98 | 39.50 | 18.40 | 1.66 | 200 | 200 | 1.00 | 0.45 | 90 |

Note:
[1] and [2] determined by POROSIMETRO Model 70 (manufactured by Acom Co.)

TABLE 2

| | | Properties of Hydroxyapatite Ceramic Materials | | | | | | |
|---|---|---|---|---|---|---|---|---|
| Classification | Raw material Specimen No. | Elementary analysis | | | Mean size of crystal (micron) | Density (g/cm$^3$) | Colour | Thermal stability[1] |
| | | Ca (%) | P (%) | Ca/P | | | | |
| Theoretical | | 39.89 | 18.43 | 1.67 | | | | |
| Present invention | 1 | 39.87 | 18.51 | 1.67 | 11 | 3.16 | white translucent | no decomposition |
| | 2 | 39.86 | 18.48 | 1.67 | 5 | 3.15 | white translucent | no decomposition |
| Comparative example | 3 | 39.85 | 18.47 | 1.67 | 2.5 | 3.02 | light blue | no decomposition |
| | 4 | 38.34 | 18.40 | 1.61 | 3 | 3.12 | white | decomposition observed |

Note:
[1] evaluated by the presence or absence of the formation of whitlockite in the specimen heated for one hour at a temperature of 1,350° C.

TABLE 3

Results of Sintering Test: amount of whitlockite

Unit (%)

| Classification Raw material | Temperature of firing (°C.) | | | |
|---|---|---|---|---|
| | 1200 | 1250 | 1300 | 1350 |
| Present invention Specimen No. 1 | 0 | 0 | 0 | 0 |
| Comparative example Specimen No. 4 | 6.0 | 41.5 | 41 | 42 |

What is claimed is:

1. A filtered, dried cake of hydroxyapatite having a structure possessing the three-dimensional order with an average opening radius of 50 to 150 Å and a pore cavity of 0.2 to 0.8 cm$^3$/g, said cake comprising, hydroxyapatite having an atomic ratio of calcium to phosphorus of 1.67 to 1.69 and a dimension including a length of 150 to 1200 Å, a width of 50 to 400 Å, a ratio of said length to said width of 3 to 10.

* * * * *